(12) United States Patent
Gartside et al.

(10) Patent No.: US 8,258,358 B2
(45) Date of Patent: Sep. 4, 2012

(54) INTEGRATED PROPYLENE PRODUCTION

(75) Inventors: Robert J. Gartside, Summit, NJ (US); Bala Ramachandran, Easton, PA (US)

(73) Assignee: Lummus Technology Inc., Bloomfield, NJ (US)

( * ) Notice: Subject to any disclaimer, the term of this patent is extended or adjusted under 35 U.S.C. 154(b) by 0 days.

(21) Appl. No.: 13/343,076

(22) Filed: Jan. 4, 2012

(65) Prior Publication Data

US 2012/0108864 A1    May 3, 2012

Related U.S. Application Data (62) Division of application No. 12/540,109, filed on Aug. 12, 2009, now Pat. No. 8,153,851.

(60) Provisional application No. 61/088,221, filed on Aug. 12, 2008.

(51) Int. Cl.
*C07C 6/04* (2006.01)
*C07C 4/02* (2006.01)

(52) U.S. Cl. .................. 585/324; 585/643; 585/648

(58) Field of Classification Search .................. 585/324, 585/643, 648

See application file for complete search history.

(56) References Cited

U.S. PATENT DOCUMENTS

| | | | |
|---|---|---|---|
| 5,026,935 | A | 6/1991 | Leyshon et al. |
| 5,080,780 | A | 1/1992 | Canzoneri et al. |
| 5,087,780 | A | 2/1992 | Arganbright |
| 5,898,091 | A | 4/1999 | Chodorge et al. |
| 6,075,173 | A | 6/2000 | Chodorge et al. |
| 6,271,430 | B2 | 8/2001 | Schwab et al. |
| 6,307,117 | B1 | 10/2001 | Tsunoda et al. |
| 6,358,482 | B1 | 3/2002 | Chodorge et al. |
| 6,580,009 | B2 | 6/2003 | Schwab et al. |
| 6,683,019 | B2 | 1/2004 | Gartside et al. |
| 6,727,396 | B2 | 4/2004 | Gartside |
| 6,777,582 | B2 | 8/2004 | Gartside et al. |
| 7,045,669 | B2 | 5/2006 | Sumner et al. |
| 7,214,841 | B2 | 5/2007 | Gartside et al. |
| 7,223,895 | B2 | 5/2007 | Sumner |

(Continued)

FOREIGN PATENT DOCUMENTS

KR    100814159 B1    3/2008

OTHER PUBLICATIONS

Cracking of pentenes to C2-C4 light olefins over zeolites and zeotypes: Role of topology and acid site strength and concentration, Bortnovsky et al., Applied Catalysis A: General, 287, 2005, 203-213.
International Search Report and Written Opinion dated Apr. 6, 2010 in corresponding International application No. PCT/US2009/053432 (12 pages).

(Continued)

*Primary Examiner* — Thuan Dinh Dang
(74) *Attorney, Agent, or Firm* — Osha Liang LLP (57) ABSTRACT

A process for the production of propylene, the process including: fractionating a hydrocarbon stream comprising n-butenes, isobutylene, and paraffins into at least two fractions including a light $C_4$ fraction comprising isobutylene and a heavy $C_4$ fraction comprising n-butenes and paraffins; contacting at least a portion of the heavy $C_4$ fraction with a metathesis catalyst to form a metathesis product comprising ethylene, propylene, $C_{4+}$ olefins, and paraffins; fractionating the metathesis product into at least four fractions including an ethylene fraction, a propylene fraction, a $C_4$ fraction comprising $C_4$ olefins and paraffins, and a $C_{5+}$ fraction; cracking the light $C_4$ fraction and the $C_{5+}$ fraction to produce a cracking product comprising ethylene, propylene, and heavier hydrocarbons; and fractionating the cracking product into at least two fractions including a light fraction comprising propylene and a fraction comprising $C_5$ to $C_6$ hydrocarbons.

18 Claims, 5 Drawing Sheets

U.S. PATENT DOCUMENTS 7,317,133 B2 1/2008 Vora et al.
2005/0080307 A1 4/2005 Voskoboynikov et al.
2008/0039667 A1 2/2008 Vora et al.
2008/0146856 A1 6/2008 Leyshon

OTHER PUBLICATIONS

International Preliminary Report on Patentability dated Feb. 15, 2011 in corresponding International application No. PCT/US2009/053432 (7 pages).

INTEGRATED PROPYLENE PRODUCTION

CROSS-REFERENCE TO RELATED APPLICATION

This application, pursuant to 35 U.S.C. §120, claims benefit to U.S. Patent application Ser. No. 12/540,109, filed Aug. 12, 2009, now U.S. Pat. No. 8,153,851, which, pursuant to 35 U.S.C. §119(e), claims priority to U.S. Provisional Application Ser. No. 61/088,221, filed Aug. 12, 2008, which is incorporated by reference in its entirety.

BACKGROUND OF DISCLOSURE

1. Field of the Disclosure

Embodiments disclosed herein relate generally to the processing of a $C_3$ to $C_6$ hydrocarbon cut from a cracking process, such as steam or fluid catalytic cracking, primarily for conversion of $C_4$ olefins to propylene via metathesis.

2. Background

In typical olefin plants, such as illustrated in U.S. Pat. No. 7,223,895, there is a front-end demethanizer for the removal of methane and hydrogen followed by a deethanizer for the removal of ethane, ethylene and $C_2$ acetylene. The bottoms from this deethanizer tower consist of a mixture of compounds ranging in carbon number from $C_3$ to $C_6$. This mixture may be separated into different carbon numbers, typically by fractionation.

The $C_3$ cut, primarily propylene, is removed as product and is ultimately used for the production of polypropylene or for chemical synthesis such as propylene oxide, cumene, or acrylonitrile. The methyl acetylene and propadiene (MAPD) impurities must be removed either by fractionation or hydrogenation. Hydrogenation is preferred since some of these highly unsaturated $C_3$ compounds end up as propylene thereby increasing the yield.

The $C_4$ cut, consisting of $C_4$ acetylenes, butadiene, iso- and normal butenes, and iso- and normal butane can be processed in many ways. A typical steam cracker $C_4$ cut contains the following components in weight %:

TABLE 1

Typical $C_4$ cut components and weight percentages.

| | |
|---|---|
| $C_4$ Acetylenes | Trace |
| Butadiene | 33% |
| 1-butene | 15% |
| 2-butene | 9% |
| Isobutylene | 30% |
| Iso- and Normal Butanes | 13% |

The components in a refinery or FCC based $C_4$ cut are similar, with the exception that the percentage of paraffins are considerably greater.

Typically, the butadiene and $C_4$ acetylenes are removed first. This can be accomplished by either hydrogenation or extraction. The product from butadiene and $C_4$ acetylene removal is designated Raffinate I. If extraction is employed, the remaining 1-butene and 2-butene remain essentially in the same ratio as that of the initial feedstock. If hydrogenation is employed, the initial product from butadiene hydrogenation is 1-butene. Subsequently, hydroisomerization occurs within the same reaction system changing the 1-butene to 2-butene. The extent of this reaction depends upon catalyst and reaction conditions within the hydrogenation system. However, it is common practice to limit the extent of hydroisomerization in order to avoid "over hydrogenation" and the production of butanes from butenes. This would represent a loss of butene feedstock for downstream operations. The butenes remaining in the mixture consist of normal olefins (1-butene, 2-butene) and iso-olefins (isobutylene). The balance of the mixture consists of both iso- and normal-butanes from the original feed plus what was produced in the hydrogenation steps and any small quantity of unconverted or unrecovered butadiene.

A Raffinate I stream can be further processed in many ways. A Raffinate II stream is by definition a stream following isobutylene removal. Isobutylene can be removed in a number of ways. It can be removed via fractionation. In fractionation isobutane will be removed along with the isobutylene. In addition, some fraction of the 1-butene will be lost as well. The resultant Raffinate II will contain primarily normal olefins and paraffins and minimal isoolefins and isoparaffins. Isobutylene can also be removed via reaction. Reactions include: reaction with methanol to form MTBE, reaction with water to form tertiary butyl alcohol, or reaction with itself to form a $C_8$ gasoline component. In all reaction cases, the paraffins are not removed, and thus the mixture will contain both normal and iso-paraffins. The paraffin content and composition of the Raffinate II impacts downstream processing options.

The butenes have many uses. One such use is for the production of propylene via metathesis. Another is for the production of ethylene and hexene via metathesis. Conventional metathesis involves the reaction of normal butenes (both 1-butene and 2-butene) with ethylene (principally the reaction of 2-butene with ethylene to form propylene). These reactions occur in the presence of a group VIA or VIIA metal oxide catalyst, either supported or unsupported. The paraffin components of the reaction feed are essentially inert and do not react, and are typically removed from the process via a purge stream in the separation system that follows the metathesis reactor. Typical catalysts for metathesis are tungsten oxide supported on silica or rhenium oxide supported on alumina. Examples of catalysts suitable for the metathesis of olefins are described in U.S. Pat. No. 6,683,019, for example. Isobutylene (isobutene) may be removed from the feedstock prior to the metathesis reaction step. The reaction of isobutylene with ethylene is non-productive and reaction with itself and/or other $C_4$'s is limited in the presence of excess ethylene. Non-productive reactions essentially occupy catalyst sites but produce no product. If allowed to remain in the feed to the metathesis unit, the concentration of this non-reactive species would build up creating capacity limitations. The reaction of 1-butene with ethylene is also non-productive. However, it is common to employ a double bond isomerization catalyst within the metathesis reactor to shift 1-butene to 2-butene and allow for continued reaction. Typical double bond isomerization catalysts include basic metal oxides (Group IIA), either supported or unsupported. Magnesium oxide and calcium oxide are examples of such double bond isomerization catalysts that may be physically admixed with the metathesis catalyst. No equivalent co-catalyst exists for the skeletal isomerization of isobutylene to normal butene. In the case of a conventional metathesis system employing both a metathesis catalyst and a co-mixed double bond isomerization catalyst, the butadiene must be removed to a level of less than 500 ppm to avoid rapid fouling of the double bond isomerization catalyst. The metathesis catalyst itself can tolerate butadiene levels up to 10,000 ppm.

In some cases, an isobutylene removal step is employed prior to metathesis. Options include reacting it with methanol to produce methyl tertiary butyl ether (MTBE) or separating the isobutylene from the butenes by fractionation. U.S. Pat. No. 6,358,482 discloses the removal of isobutylene from the $C_4$ mixture prior to metathesis. This scheme is further reflected in U.S. Pat. Nos. 6,075,173 and 5,898,091. U.S. Pat. No. 6,580,009 discloses a process for the production of propylene and hexene from a limited ethylene fraction. For molar ratios of ethylene to butenes (expressed as n-butenes) from 0.05 to 0.60, the inventors utilize a Raffinate II stream as the $C_4$ feedstock.

The typical metathesis process takes the Raffinate I feedstock and removes the majority of the isobutylene via fractionation, as described above to form a Raffinate II. In this step, the isobutene is removed as well plus some quantities of normal butenes, dependent upon the fractionation conditions. The Raffinate II is then admixed with ethylene, passed through guard beds to remove poisons, vaporized and preheated and fed to the metathesis reactors. The operating conditions are typically 300° C. and 20 to 30 bar pressure. The reactor effluent following heat recovery is then separated in a fractionation system. First the ethylene is recovered overhead in a first tower and recycled to the reactor system. The tower bottoms are then sent to a second tower where the propylene is recovered overhead. A side draw is taken containing the majority of the unconverted $C_4$ components and recycled to the reactor. The tower bottoms containing the $C_5$ and heavier products plus $C_4$ olefins and paraffins are sent to purge. The purge rate is typically fixed to contain sufficient $C_4$ paraffins to avoid their buildup in the reactor recycle stream. In some cases, a third tower is employed on the tower bottoms stream to separate the $C_4$ components overhead and the $C_5$ and heavier components as a bottoms stream.

U.S. Pat. No. 6,271,430 discloses a two-step process for the production of propylene. The first step consists of reacting 1-butene and 2-butene in a raffinate II stream in an autometathesis reaction to form propylene and 2-pentene. The products are then separated in the second step. The third step reacts specifically the 2-pentene with ethylene to form propylene and 1-butene. This process utilizes the isobutylene free raffinate II stream. The pentenes recycled and reacted with ethylene are normal pentenes (2-pentene).

Isobutylene removal from the $C_4$ stream can also be accomplished by employing a combined catalytic distillation hydroisomerization deisobutyleneizer system to both remove the isobutylene and recover n-butenes at high efficiency by isomerizing the 1-butene to 2-butene with known isomerization catalysts and thus increasing the volatility difference. This technology combines conventional fractionation for isobutylene removal with hydroisomerization within a catalytic distillation tower. In U.S. Pat. No. 5,087,780 to Arganbright, 2-butene is hydroisomerized to 1-butene as the fractionation occurs. This allows greater than equilibrium amounts of 1-butene to be formed as the mixture is separated. Similarly, 1-butene can be hydroisomerized to 2-butene in a catalytic distillation tower. In separating a $C_4$ stream containing isobutylene, 1-butene, and 2-butene (plus paraffins), it is difficult to separate isobutylene from 1-butene since their boiling points are very close. By employing simultaneous hydroisomerization of the 1-butene to 2-butene with fractionation of isobutylene, isobutylene can be separated from the normal butenes at high efficiency.

The metathesis reaction described above is equimolar, i.e., one mole of ethylene reacts with 1 mole of 2-butene to produce 2 moles of propylene. However, commercially, in many cases, the quantity of ethylene available is limited with respect to the quantity of butenes available. In addition, the ethylene is an expensive feedstock and it is desired to limit the quantities of ethylene used. As the ratio of ethylene to butenes is decreased, there is a greater tendency for the butenes to react with themselves which reduces the overall selectivity to propylene.

The metathesis catalysts and the double bond isomerization catalysts are quite sensitive to poisons. Poisons include water, $CO_2$, oxygenates (such as MTBE), sulfur compounds, nitrogen compounds, and heavy metals. It is common practice to employ guard beds upstream of the metathesis reaction system to insure the removal of these poisons. It does not matter if these guard beds are directly before the metathesis reaction system or further upstream as long as the poisons are removed and no new poisons are subsequently introduced.

Metathesis reactions are very sensitive to the location of the olefin double bond and the stereo-structure of the individual molecules. During the reaction, the double bond on each pair of olefins adsorb on the surface and exchange double bond positions with the carbon groups on either sides of the double bonds. Metathesis reactions can be classified as productive, half productive or non-productive. As described above, non-productive reactions result in essentially no reaction taking place. When the double bonds shift with metathesis reaction, the new molecules are the same as the originally adsorbed molecules thus no productive reaction occurs. This is typical for reactions between symmetric olefins or reactions between ethylene and alpha olefins. If fully productive reactions occur, new products are generated no matter which orientation the molecules occupy the sites. The reaction between ethylene and 2-butene to form two propylene molecules is a fully productive reaction. Half productive reactions are sterically inhibited. If the pair of olefins adsorb in one orientation (typically the cis position with respect to the attached R groups), when the double bonds shift, new products are formed. Alternately if they adsorb in a different steric configuration (the trans position), when the bonds shift, the identical olefins are formed and thus no new products are formed. The various metathesis reactions proceed at different rates (a fully productive reaction is usually faster than a half productive reaction). Table 2 summarizes the reactions between ethylene and various butenes and the reactions between the butenes themselves.

The reactions listed in Table 2 represent the base reaction with ethylene (reaction 1, 4 and 5) as well as the reactions between the various $C_4$ olefins. It is especially important to make a distinction between the selectivity to propylene from total $C_4$ olefins (including isobutylene) and the selectivity to propylene from the normal $C_4$ olefins involved in the reaction. The reaction of isobutylene with 2-butene (reaction 6) produces propylene and a branched $C_5$ molecule. For this reaction, propylene is produced at 50 molar % selectivity from total $C_4$'s (similar to reaction 2) but at a 100 molar % selectivity from the normal $C_4$ (2-butene). For the purposes of definitions, conventional metathesis is defined as the reaction of the $C_4$ olefin stream with ethylene. However, the $C_4$ stream can also react in the absence of ethylene as a feedstock. This reaction is called auto or self metathesis. In this case, reactions 2, 3, 6, and 7 are the only possible reactions and will occur at rates dependent upon the feedstock composition.

TABLE 2

| No. | Reaction | Type | Rate | Molar % Selectivity ($C_3H_6$ from total $C_4$s) | Molar % Selectivity ($C_3H_6$ from n-$C_4$s) |
|---|---|---|---|---|---|
| 1 | 2-butene + ethylene → 2 propylene (Conventional Metathesis) | Fully Productive | Fast | 100 | 100 |

TABLE 2-continued

| No. | Reaction | Type | Rate | Molar % Selectivity ($C_3H_6$ from total $C_4$s) | Molar % Selectivity ($C_3H_6$ from n-$C_4$s) |
|---|---|---|---|---|---|
| 2 | 1-butene + 2-butene → Propylene + 2-pentene | Fully Productive | Fast | 50 | 50 |
| 3 | 1-butene + 1-butene → Ethylene + 3-hexene | Half Productive | Slow | 0 | 0 |
| 4 | Isobutylene + Ethylene → No reaction | Non-productive | No Reaction | — | — |
| 5 | 1-butene + ethylene → No reaction | Non-productive | No Reaction | | |
| 6 | Isobutylene + 2-butene → Propylene + 2-methyl 2-butene | Fully Productive | Fast | 50 | 100 |
| 7 | Isobutylene + 1-butene → ethylene + 2-methyl 2 pentene | Half productive | Slow | 0 | 0 |

In conventional metathesis, the focus is to maximize reaction 1 to produce propylene. This will maximize the selectivity to propylene. As such, excess ethylene is used to reduce the extent of the reactions of butenes with themselves (reactions 2, 3, 6, and 7). The theoretical ratio is 1/1 molar or 0.5 weight ratio of ethylene to n-butenes but it is common in conventional metathesis to employ significantly greater ratios, typically, 1.3 or larger molar ratio to minimize reactions 2, 3, 6 and 7. Under conditions of excess ethylene, and due to the fact that both isobutylene and 1-butene do not react with ethylene (see reactions 4 and 5), two process sequences are employed. First, the isobutylene is removed prior to metathesis. If isobutylene is not removed, it will build up as the n-butenes are recycled to achieve high yield. Second, 1-butene is isomerized to 2-butene by including a double bond isomerization catalyst such as magnesium oxide admixed with the metathesis catalyst. Note that this catalyst will not cause skeletal isomerization (isobutylene to normal butylenes) but only shift the double bond from the 1 position to the 2 position for the normal butenes. Thus by operating with excess ethylene, eliminating isobutylene from the metathesis feed prior to reaction, and employing a double bond isomerization catalyst, reaction 1 is maximized. Note, however, that by removing the isobutylene, potential production of propylene or other products is lost.

When there is limited or no fresh ethylene (or excess butylenes for the ethylene available), there are currently two options available for propylene production. In these cases, the first option will first remove the isobutylene and then process the normal butenes with whatever ethylene is available. The entire n-butenes-only mixture is subjected to metathesis with the available ethylene. Ultimately, if there is no fresh ethylene available, the $C_4$'s react with themselves (auto metathesis). Under low ethylene conditions, reactions 2, 3, 6 and 7 will occur, all leading to a lower propylene selectivity (50% or lower versus 100% for reaction 1). The lower selectivity results in lower propylene production. Note that reactions 6 and 7 will be minimized as a result of the removal of isobutylene (to low levels but not necessarily zero). Alternately, the molar flows of ethylene and butenes can be matched by limiting the flow of butenes to produce conditions where there is a high selectivity of the normal butenes to propylene via reaction 1. By limiting the flow of n-butenes to match ethylene, the production of propylene is limited by the reduced butenes flow.

Pentenes and some hexenes are formed to some extent in the conventional metathesis case with low ethylene via reactions 2 and 3. The volume of these components will depend upon the ethylene/n-butenes ratio with a lower ratio producing more $C_5$ and $C_6$ components. In the conventional prior art case where isobutylene is removed before any metathesis, these $C_5$ and $C_6$ olefins are normal olefins since no skeletal isomerization occurs. It is possible to recycle these olefins back to the metathesis step where, for example, the reaction with ethylene and 2-pentene will occur yielding propylene and 1-butene. The 1-butene is recovered and recycled. Note however, with limited ethylene, reaction 1 can occur only to the limit of the ethylene availability. Ultimately these non-selective byproducts, pentenes and hexenes, must be purged from the system.

U.S. Pat. No. 6,777,582 discloses a process for the auto-metathesis of olefins to produce propylene and hexene. Therein, auto-metathesis of a mixed normal butenes feed in the presence of a metathesis catalyst operates without any ethylene in the feed mix to the metathesis reactor. Some fraction of the 2-butene feed may be isomerized to 1-butene and the 1-butene formed plus the 1-butene in the feed react rapidly with the 2-butene to form propylene and 2-pentene. The feed to the reactor also includes the recycle of the 2-pentene formed in the reactor with unreacted butenes to simultaneously form additional propylene and hexene. The 3-hexene formed in the reaction may be isomerized to 1-hexene.

In U.S. Pat. No. 6,727,396, ethylene and hexene-1 are produced from butene-1 by metathesis of butene-1 and isomerization of the hexene-3 produced therein to hexene-1. The initial starting material is a mixed butene stream wherein butene-1 is isomerized to butene-2 with isobutylene being separated therefrom, followed by isomerization of butene-2 to butene-1, with the butene-1 being the feed to the metathesis.

In U.S. Pat. No. 7,214,841, the $C_4$ cut from a hydrocarbon cracking process is first subjected to auto-metathesis prior to any isobutylene removal and without any ethylene addition, favoring the reactions which produce propylene and pentenes. The ethylene and propylene produced are then removed leaving a stream of the C.sub.4's and heavier components. The C.sub.5 and heavier components are then removed leaving a mixture of 1-butene, 2-butene, isobutylene, and iso- and normal butanes. The isobutylene is next removed preferably by a catalytic distillation hydroisomerization de-isobutyleneizer. The isobutylene-free $C_4$ stream is then mixed with the product ethylene removed from the auto-metathesis product together with any fresh external ethylene needed and subjected to conventional metathesis producing additional propylene.

Another use of the $C_4$ olefin stream is as a feedstock to an olefin cracking process, where the olefins are reacted with themselves over a zeolitic catalyst to produce a mixture comprising ethylene, propylene, and aromatics (such as benzene). Similar to the metathesis process, the paraffins are inert in this cracking process and must be removed from the process via a purge stream. U.S. Pat. No. 6,307,117 and U.S. Patent Application Publication No. 20050080307 both describe such a process. A mixture of typically $C_4$ to $C_6$ olefins as well as paraffins is vaporized and fed to a reactor filled with a crystalline zeolitic catalyst and operating at a temperature between 450 and 600° C. and a pressure between 10 and 70 psia. The reactor effluent is first sent to a compression step. The cracking reactor system operates at relatively low pressure to avoid fouling of the catalyst in the cracking reactor. In order to reduce the energy costs due to refrigeration in the subsequent separation system, the pressure is typically increased to pressures on the order of 12 to 25 barg. This allows the subsequent fractionating towers to utilize cooling water instead of refrigeration in the overhead condensation step. The compression effluent is then sent to a separation system where the ethylene and propylene are recovered along with an aromatics stream. The ethylene and propylene is recovered overhead in a first tower. Unlike metathesis, these products contain sufficient quantities of ethane and propane that additional purification of this stream is necessary. This can be accomplished by additional fractionation or by utilizing the recovery system of an adjacent facility such as an olefins plant. The tower bottoms contains $C_4$, $C_5$ and $C_{6+}$ paraffins and aromatics. This is sent to a second tower. The overhead is a $C_4/C_5$ stream and the highly aromatic $C_{6+}$ stream is the bottoms product. The unconverted $C_4$ and $C_5$ products are typically recycled. The cracking process can handle both iso and normal olefins with equivalent efficiency. There is no need to remove isobutylene for example from the feed to maximize propylene production.

As described above, there is considerable interest in the processing of $C_4$, $C_5$, and heavier olefin streams to produce lighter olefins, such as propylene. Accordingly, there exists a significant need for processes that may result in the production of high purity propylene from such olefin-containing streams at low cost and low energy.

SUMMARY OF THE DISCLOSURE

In one aspect, embodiments disclosed herein relate to a process for the production of propylene, the process including: fractionating a hydrocarbon stream comprising n-butenes, isobutylene, and paraffins into at least two fractions including a light $C_4$ fraction comprising isobutylene and a heavy $C_4$ fraction comprising n-butenes and paraffins; contacting at least a portion of the heavy $C_4$ fraction with a metathesis catalyst to form a metathesis product comprising ethylene, propylene, $C_{4+}$ olefins, and paraffins; fractionating the metathesis product into at least four fractions including an ethylene fraction, a propylene fraction, a $C_4$ fraction comprising $C_4$ olefins and paraffins, and a $C_{5+}$ fraction; cracking the light $C_4$ fraction and the $C_{5+}$ fraction to produce a cracking product comprising ethylene, propylene, and heavier hydrocarbons; and fractionating the cracking product into at least two fractions including a light fraction comprising propylene and a fraction comprising $C_5$ to $C_6$ hydrocarbons.

In another aspect, embodiments disclosed herein relate to a process for the production of propylene, the process including: contacting a mixed-$C_4$ stream comprising n-butenes, isobutylene, and paraffins with a metathesis catalyst whereby auto-metathesis occurs including the reaction of isobutylene with n-butenes to form an auto-metathesis product comprising ethylene, propylene, and heavier olefins including unreacted isobutylene and paraffins; fractionating the auto-metathesis product into at least four fractions including an ethylene fraction, a propylene fraction, a $C_{5+}$ fraction, and a $C_4$ fraction containing n-butenes, isobutylene, and paraffins; fractionating the $C_4$ fraction into at least two fractions including a light $C_4$ fraction comprising isobutylene and a heavy $C_4$ fraction comprising n-butenes and paraffins; contacting at least a portion of the heavy $C_4$ fraction and ethylene with a metathesis catalyst to form a metathesis product comprising ethylene, propylene, $C_{4+}$ olefins, and paraffins; feeding the metathesis product to the fractionating the auto-metathesis product; cracking the $C_{5+}$ fraction to produce a cracking product comprising ethylene, propylene, and heavier hydrocarbons; and fractionating the cracking product into at least two fractions including a light fraction comprising propylene and a fraction comprising $C_5$ to $C_6$ hydrocarbons.

Other aspects and advantages will be apparent from the following description and the appended claims.

DETAILED DESCRIPTION

In one aspect, embodiments herein relate to the processing of a $C_4$ to $C_6$ hydrocarbons to form lighter olefins, such as ethylene and propylene. In another aspect, embodiments disclosed herein relate to the conversion of $C_4$ to $C_6$ olefins to ethylene and propylene via an integrated metathesis and cracking process. More specifically, embodiments disclosed herein relate to fractionation of a mixed $C_4$ stream to form a light $C_4$ fraction including isobutylene and a heavy $C_4$ fraction including 2-butene, metathesis of 2-butenes in the heavy $C_4$ fraction, and the subsequent cracking of a combined stream including the light $C_4$ fraction and $C_{5+}$ metathesis products to produce propylene at high yields.

In another aspect, embodiments disclosed herein relate to the auto-metathesis of the $C_4$ feedstock without ethylene to form a reaction effluent comprising ethylene, propylene, unreacted $C_4$ olefins, $C_4$ paraffins and $C_5/C_6$ normal and iso-olefins. In some embodiments, isobutylene is not removed from the feedstock to that auto-metathesis reaction. The reactor effluent is first fractionated to recover light ethylene and propylene products. The remaining effluent is subjected to continued fractionation to recover a $C_4$ product overhead and a $C_5$ and heavier stream. The $C_4$ overhead stream is fractionated to create a light $C_4$ fraction comprising isobutylene and isobutene, and a heavy $C_4$ stream comprising mostly normal butenes and normal butane. The heavy $C_4$ stream is admixed with ethylene and subjected to metathesis. The products of this metathesis reaction are mixed with the products of the first auto-metathesis reaction and go to the common separation system. Some or all of the $C_5$ and heavier stream is fed to the cracking reactor along with some or all of the overhead from the $C_4$ fractionation tower. The effluent from the cracking reactor contains ethylene, propylene, and aromatics.

In other embodiments, the light gases from the cracking reaction may be sent to the separation zone of the metathesis reaction system. In this manner the ethylene produced in the cracking reaction section may be used to provide additional ethylene for the metathesis reaction, and reduce or minimize the required feed ethylene.

The mixed $C_4$ feed to processes disclosed herein may include $C_3$ to $C_{6+}$ hydrocarbons, including $C_4$, $C_4$ to $C_5$, and $C_4$ to $C_6$ cracker effluents, such as from a steam cracker or a fluid catalytic cracking (FCC) unit. Other refinery hydrocarbon streams containing a mixture of $C_4$ olefins may also be used. When $C_3$, $C_5$ and/or $C_6$ components are present in the feed, the stream may be pre-fractionated to result in a primary $C_4$ cut, a $C_4$ to $C_5$ cut, or a $C_4$ to $C_6$ cut.

$C_4$ components contained in the feed stream may include n-butane, isobutane, isobutene, 1-butene, 2-butene, and butadiene. In some embodiments, the mixed $C_4$ feed is pretreated to provide a 1-butene feed for the metathesis reaction. For example, when butadiene is present in the $C_4$ feed, the butadiene may be removed via hydrogenation or extraction. In other embodiments, the mixed butenes feed following or in conjunction with butadiene hydrogenation may be subjected to hydroisomerization conditions to convert 1-butene to 2-butene, with isobutylene being separated from a 2-butene stream by fractionation. The 2-butene stream may then be isomerized back to 1-butene in a subsequent step for use as feed to the metathesis portion of the processes disclosed herein.

The 1-butene may then be contacted with a metathesis catalyst to convert at least a portion of the 1-butene to ethylene, propylene, and $C_5$ to $C_6$ metathesis products. In some embodiments, the 1-butene may be subject to auto-metathesis, and in other embodiments may be subject to conventional metathesis, where ethylene is co-fed with the 1-butene to the metathesis reactor.

The metathesis reactor may operate at a pressure between 2 and 40 atmospheres in some embodiments, and between 5 and 15 atmospheres in other embodiments. The metathesis reactor may be operated such that the reaction temperature is within the range from about 50° C. to about 600° C.; within the range from about 200° C. to about 450° C. in other embodiments; and from about 250° C. to about 400° C. in yet other embodiments. The metathesis reaction may be performed at a weight hourly space velocity (WHSV) in the range from about 3 to about 200 in some embodiments, and from about 6 to about 40 in other embodiments.

The reaction may be carried out by contacting the olefin(s) with the metathesis catalyst in the liquid phase or the gas phase depending on structure and molecular weight of the olefin(s). If the reaction is carried out in the liquid phase, solvents or diluents for the reaction can be used. Aliphatic saturated hydrocarbons, e.g., pentanes, hexanes, cyclohexanes, dodecanes and aromatic hydrocarbons such as benzene and toluene are suitable. If the reaction is carried out in the gaseous phase, diluents such as saturated aliphatic hydrocarbons, for example, methane, ethane, and/or substantially inert gases, such as nitrogen and argon, may be present. For high product yield, the reaction may be conducted in the absence of significant amounts of deactivating materials such as water and oxygen.

The contact time needed to obtain a desirable yield of metathesis reaction products depends upon several factors such as the activity of the catalyst, temperature, pressure, and the structure of the olefin(s) to be metathesized. Length of time during which the olefin(s) are contacted with catalyst can conveniently vary between 0.1 seconds and 4 hours, preferably from about 0.5 sec to about 0.5 hrs. The metathesis reaction may be conducted batch-wise or continuously with fixed catalyst beds, slurried catalyst, fluidized beds, or by using any other conventional contacting techniques.

The catalyst contained within the metathesis reactor may be any known metathesis catalyst, including oxides of Group VIA and Group VIIA metals on supports. Catalyst supports can be of any type and could include alumina, silica, mixtures thereof, zirconia, and zeolites. In addition to the metathesis catalyst, the catalyst contained in the metathesis reactor may include a double bond isomerization catalyst such as magnesium oxide or calcium oxide. In some embodiments, the catalyst may include a promoter to reduce acidity; for example, an alkali metal (sodium, potassium or lithium), cesium, a rare earth, etc.

The effluent from the metathesis reactor may be sent to a separation system to separate the metathesis effluent into carbon number groups by technology well known in the art. For example, the products of the separation system may include an ethylene stream, a propylene stream, a $C_4$ stream, and a $C_{5+}$ stream. The propylene stream may be recovered as a product stream, which may also undergo further purification steps to obtain a high purity propylene product. The $C_4$ stream may be recycled back to the metathesis reactor or a pre-treatment stage, such as isomerization or fractionation. The ethylene stream may be recovered as a product stream or may be recycled back to the metathesis reactor for use as an ethylene feedstock for the conventional metathesis reaction.

The $C_{5+}$ fraction recovered from separation of the metathesis reactor effluent may be combined with isobutene, such as contained in a light $C_4$ fraction resulting from pre-separation of a mixed $C_4$ cut, and fed to a cracking unit to produce additional ethylene and propylene. In some embodiments, additional $C_5$ and/or $C_6$ fractions, such as resulting from pre-fractionation of a $C_4$-$C_6$ cut to result in the metathesis butene feed, may also be fed to the cracking unit. In the cracking unit, the mixed feed may be heated to a temperature in the range of 150° C. to about 1000° C., sufficient to crack the $C_4$ to $C_6$ hydrocarbons to form ethylene and propylene, among other products. The cracking may be performed using thermal cracking, steam cracking, catalytic cracking, or a combination thereof. In some embodiments, the cracking is catalytic and is performed in the presence of a crystalline zeolitic catalyst.

The cracking reactor may operate at a pressure between 1 and 20 atmospheres in some embodiments, and between 2 and 110 atmospheres in other embodiments. The cracking reactor may be operated such that the reaction temperature is within the range from about 150° C. to about 1000° C.; within the range from about 300° C. to about 800° C. in other embodiments; and from about 450° C. to about 600° C. in yet other embodiments. The cracking reaction may be performed in the presence of a crystalline zeolitic catalyst in some embodiments, ZSM-5 zeolitic catalyst in other embodiments, and in the presence of a ZSM-5 zeolitic catalyst with a Si/Al ratio of greater than 50 in some embodiments, and a Si/Al ratio of greater than 200 in yet other embodiments.

Effluent from the cracking reactor may be sent to a separation system to separate the metathesis effluent into carbon number groups by technology well known in the art. For example, products from the cracking unit may include ethylene, propylene, $C_4$s, $C_5$s, $C_6$s, as well as various aromatics. Ethylene may be recovered from the separation system as a product or may be recycled to the metathesis reactor as an ethylene feedstock for the conventional metathesis reaction.

Propylene may be recovered as a product stream, which may also undergo further purification steps along with the metathesis propylene stream to obtain a high purity propylene product. The $C_4$ stream may be recycled back to the metathesis reactor, a pre-treatment stage upstream of the metathesis reactor, or to the cracking unit. Similarly, the $C_5$ and $C_6$ fractions may be recycled to pre-fractionation, to the metathesis unit, or to the cracking unit.

Integration of metathesis and cracking, as described above, may result in additional yield of propylene as compared to cracking or metathesis alone. For example, processes according to embodiments disclosed herein may yield 10% or more additional propylene as compared to metathesis alone; an additional 15% propylene in other embodiments; and an additional 20% propylene in yet other embodiments, as compared to metathesis alone. Alternatively, the integration of metathesis and cracking may result in a similar amount of propylene production while using a reduced amount of ethylene feedstock.

In some embodiments, both auto-metathesis and conventional metathesis may be performed. For example, an initial auto-metathesis step may be purposely utilized, where isobutylene may be reacted with the normal butenes, and isobutylene conversions can reach 50 or 60%. The products from the reaction of isobutylene with 1-butene may include ethylene and 2-methyl 2-pentene while the products with 2-butene may include propylene and 2-methyl 2-butene. These auto-metathesis reactions may be used in combination with a second conventional metathesis reaction system and a modified fractionation/isobutylene removal sequence to result in a desired production of ethylene and propylene from the entire butenes stream.

In some embodiments, an olefin feed to a conventional metathesis reactor may include essentially pure normal butenes. This can be any mixture of 1-butene and 2-butene and may also contain $C_4$ paraffins as a feed diluent. In some embodiments, the isobutene content, based on a combined amount of olefins in the feed mixture; may be less than 10%; less than 5% in other embodiments; less than 2% in other embodiments; and less than 1% in yet other embodiments.

In other embodiments, isobutene separation specifications in the pre-fractionation stage may be relaxed, thus allowing some flexibility for ethylene feed to the metathesis reactor. For example, feeding some isobutene, such as up to an isobutene concentration in the mixed $C_4$ feed of about 15%, to the metathesis reactor will allow the reduction in the overall energy costs as the fractionation requirements are reduced. This flexibility may advantageously allow for lower capital costs, due to the relaxed separation requirements, as well as the potential for the integrated metathesis-cracking process according to embodiments disclosed herein to operate with low or no net ethylene consumption. In some embodiments, a ratio of ethylene to butenes in a conventional metathesis reactor feed may range from about 0.1 to about 2.5. In other embodiments, a ratio of ethylene to butenes in a conventional metathesis reactor feed may range from about 0.8 to about 2.0; and from about 1.5 to about 2.0 in yet other embodiments.

Figure 1:
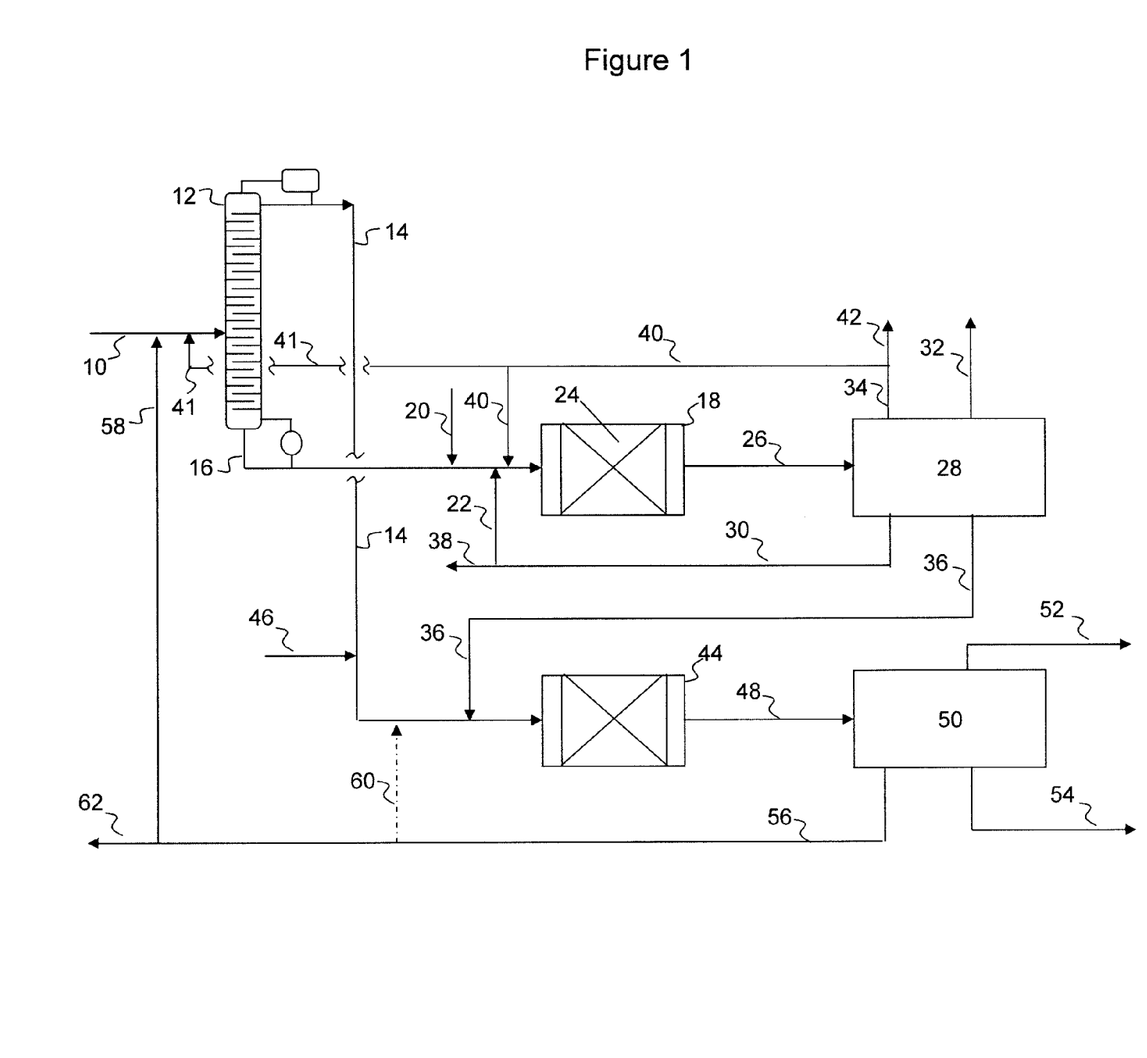
FIG. 1 is a simplified process flow diagram of a process for producing propylene according to embodiments disclosed herein.

Referring now to FIG. 1, a simplified process flow diagram of a process for producing propylene according to embodiments disclosed herein is illustrated. A mixed $C_4$ stream containing n-butenes, isobutylene, and paraffins may be fed via flow line 10 to a fractionator 12, where the $C_4$s may be fractionated into at least two fractions, including a light $C_4$ fraction, including isobutylene, and a heavy $C_4$ fraction, including n-butenes. The light $C_4$ fraction may be recovered from fractionator 12 as an overheads fraction via flow line 14. Fractionator 12 may be either a conventional fractionation tower or may be a catalytic distillation fractionation tower wherein a catalyst is utilized to isomerizes 1-butene to 20butene and hydrogenate butadiene to 1- or 2-butene while simultaneously separating the $C_4$ stream into the light $C_4$ and heavy $C_4$ fractions.

The heavy $C_4$ fraction may be recovered as a bottoms fraction via flow line 16 and fed to metathesis reactor 18. When used, ethylene may be co-fed to reactor 18 via flow lines 20 and/or 22. Metathesis reactor 18 may contain one or more beds 24 of a conventional metathesis or an auto-metathesis catalyst, with or without isomerization functionality, suitable for converting at least a portion of the linear butenes in the heavy $C_4$ fraction, with or without co-fed ethylene, to ethylene and propylene.

Effluent from metathesis reactor 18 may be fed via flow line 26 to a separation system 28, which may include, for example, distillation apparatus for separating the effluent into carbon number groups. As illustrated, separation system 28 may fractionate the metathesis product into at least four fractions, including an ethylene-containing fraction recovered vial flow line 30, a propylene-containing fraction recovered via flow line 32, a $C_4$ fraction recovered via flow line 34, and a $C_{5+}$ fraction recovered via flow line 36. The $C_5$ fraction 36 may contain $C_4$ components in addition to $C_5$ and heavier components.

A portion of the $C_2$ fraction recovered via flow line 30 may be purged from the system via flow line 38. The purge from line 38 is utilized primarily to purge trace components that may exist in the ethylene stream, including but not limited to hydrogen, methane, and/or ethane. If desired, at least a portion of the ethylene recovered via flow line 30 may be recycled as ethylene feed via flow line 22 to metathesis reactor 18.

The $C_4$ fraction recovered via flow line 34 may be recycled to metathesis reactor 18 via flow line 40. In some embodiments, at least a portion of the $C_4$ fraction may be recycled to fractionator 12 via flow line 41. In some embodiments, at least a portion of the $C_4$ fraction may be purged, if necessary, via flow line 42. The purge via line 42 may serve to purge $C_4$ paraffins from the system that could otherwise build up to substantial levels as the recycle is increased to allow for high overall conversion of the $C_4$ olefins. Typically, stream 34 may contain between 30 and 60% paraffins as a result of the recycle buildup of paraffins within the system.

Although not illustrated, the $C_4$ fraction recovered via flow line 34 may alternatively be fed to a downstream cracking unit, as described below.

The light $C_4$ fraction, including isobutylene, in flow line 14 and the $C_{5+}$ fraction recovered via flow line 36 may be fed to a cracking unit 44. Additionally, additional $C_5$ and/or $C_6$ components, such as from a pre-fractionation of a $C_4$ to $C_6$ cut (not shown), may be fed via flow line 46 to cracking unit 44. In cracking unit 44, the hydrocarbons are subjected to elevated temperatures, as described above, to crack the hydrocarbons to form propylene and ethylene, among other components.

Effluent from cracking unit 44 may be fed via flow line 48 to a separation system 50, which may include, for example, distillation apparatus for separating the effluent into carbon number groups. Separation system 50 may fractionate the cracking product into at least two fractions, such as a lights fraction including propylene, and a heavy fraction including $C_5$ and $C_6$ hydrocarbons, for example. As illustrated, separation system 50 may fractionate the cracking product into at least three fractions, including an ethylene-containing fraction recovered vial flow line 52, a propylene-containing fraction recovered via flow line 54, and a $C_{4+}$ fraction recovered via flow line 56. If necessary, the $C_{4+}$ fraction may be further separated into a $C_4$ fraction, a $C_5$ to $C_6$ fraction, and an aromatics fraction. A portion of the $C_{4+}$ fraction may be recycled to fractionator 12. Alternatively, a portion of the $C_{4+}$ fraction, such as $C_5$ to $C_6$ hydrocarbons, may be recycled to the cracking unit via flow line 60; in some embodiments, a portion of the $C_{4+}$ fraction, such as aromatics, may be purged via flow line 62.

In some embodiments, the ethylene-containing stream 52 may be to the metathesis reaction system for reaction with the $C_4$ olefins in metathesis reactor 18. In other embodiments the propylene in stream 54 may be admixed with the propylene in stream 32 to form propylene product. In further embodiments, the separation system 50 may produce a mixed ethylene/propylene stream instead of separate streams 52 and 54. The mixed ethylene/propylene stream could then be admixed with the metathesis reactor effluent 26 to utilize the common ethylene and propylene fractionation systems within separation system 28 and thus reduce capital and utility costs.

Figure 2:
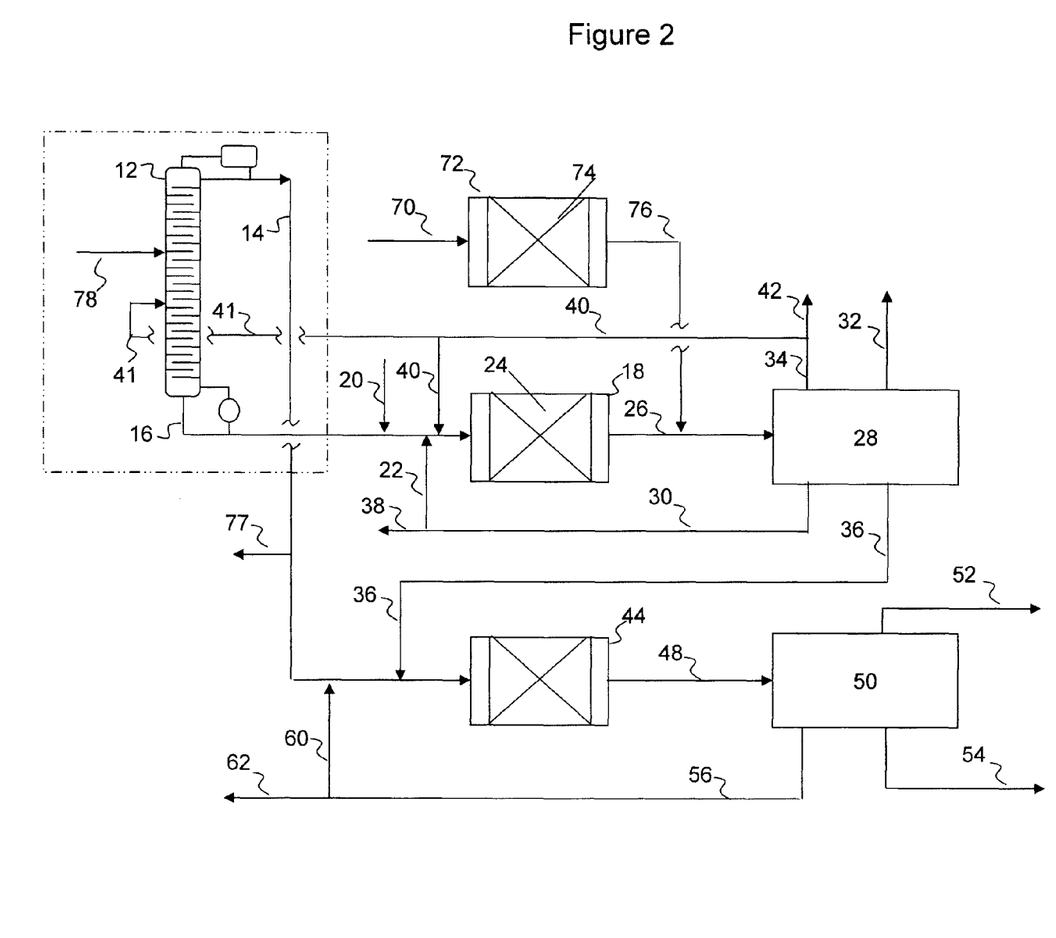
FIG. 2 is a simplified process flow diagram of a process for producing propylene according to embodiments disclosed herein.

Referring now to FIG. 2, where like numerals represent like parts, a simplified process flow diagram of a process for producing propylene according to embodiments disclosed herein is illustrated. In this embodiment, a mixed $C_4$ feedstock 70 containing both normal butenes and isobutylene along with paraffins is fed to an auto-metathesis reactor 72 containing at least one bed 74 of auto-metathesis catalyst. Contact of the butenes and isobutylene with the auto-metathesis catalyst may produce propylene and both n-pentenes/hexenes and iso-pentenes/hexenes. Importantly, to the extent that isobutylene is present, the selectivity of propylene from the n-butenes may be as high as 100%, as shown in Table 2. Further, to the extent produced from the auto-metathesis, ethylene in the auto-metathesis effluent may be available for recycle via flow line 30 for use in the conventional metathesis unit 18.

Following the auto-metathesis reaction, effluent from the auto-metathesis reactor 72 may be fed via flow line 76 along with conventional metathesis effluent recovered from reactor 18 via flow line 26 to separation unit 28, producing carbon number fractions as described with respect to FIG. 1.

In separation system 28, the $C_4$ fraction contains unreacted $C_4$ olefins and any $C_4$ paraffins found in the mixed feed 70. The composition has been considerably altered due to the reaction of the olefins in the auto-metathesis reactor 72. This stream is sent fractionator 12. In fractionator 12, the $C_4$ stream is separated into a light $C_4$ fraction, recovered via line 14 and containing unreacted isobutylene, isobutene and some fraction of normal butenes and normal butane, and a heavy C4 fraction recovered via line 16 and containing primarily normal butenes and normal butane. Stream 77 can allow for the purge of the paraffins from the metathesis system. The heavy $C_4$ fraction from fractionator 12 is directed to metathesis reactor 18 via line 16. This stream may be admixed with ethylene via line 20 or line 22. Note that since a large fraction of the $C_4$ olefins have reacted in auto-metathesis reactor 72, a considerably reduced amount of ethylene is required to be added via lines 20 or 22 to maintain an equivalent ethylene/butenes ratio for the metathesis reactor 18.

The $C_5$ fraction recovered from separation unit 28 will contain pentenes and hexenes (both iso and normal). This fraction may be fed to the cracking reactor 44 via line 36, as described for FIG. 1. This stream will not contain substantial amounts of $C_4$ paraffins as is the case for line 34. By employing the metathesis reaction and by producing $C_5$ and $C_6$ olefins from the reaction of the $C_4$ olefins, the process has used reaction to separate the paraffins from the olefins prior to entering cracking reaction system 44. As discussed above, the cracking reaction system operates at low pressure and must employ a compression step to achieve economic separation of products following the reactor. To the extent that paraffins are contained in the feedstock, these will significantly increase the compression utilities and capital cost. As the unreacted olefins are recycled back to the cracking reactor via line 60, the concentration of paraffins will build up, and the compression debit increases dramatically. By integrating the metathesis reaction system with the cracking reactor system, the paraffins can be effectively removed at the higher pressure of the metathesis system, employing pumps as opposed to compressors, and thus the overall utilities of the system dramatically reduced. This is true for both the integration of FIG. 1 and the integration of FIG. 2.

As described for FIG. 1, the ethylene stream 52 and/or the propylene stream 54 from separation system 28 can be integrated with the separation system for the auto-metathesis/metathesis reactor systems.

In some embodiments, there may be additional fresh mixed $C_4$ feed introduced to the system at fractionator 12, such as via flow line 78, as opposed to all of the $C_4$ feed entering the system via line 70. It would be characteristic of this stream to contain high concentrations of paraffins that would thus be purged via line 77 prior to entering the reactor 18 and separation system 28.

In some embodiments, $C_5$ and heavier components may be allowed to remain with the mixed $C_4$ fraction fed to fractionator 12. Isopentenes formed in the auto-metathesis step could be subsequently reacted with ethylene in the conventional metathesis reactor. Isobutylene would be re-formed by reaction with feed ethylene and/or product propylene. Note, however, that to the extent that the normal pentenes are allowed to pass to the conventional metathesis, they react to form propylene and normal butenes which is a desirable reaction. At this point, there is a mixture of n-butenes, isobutylene, and both iso and normal butanes and some $C_5$ and heavier material.

Figure 3:
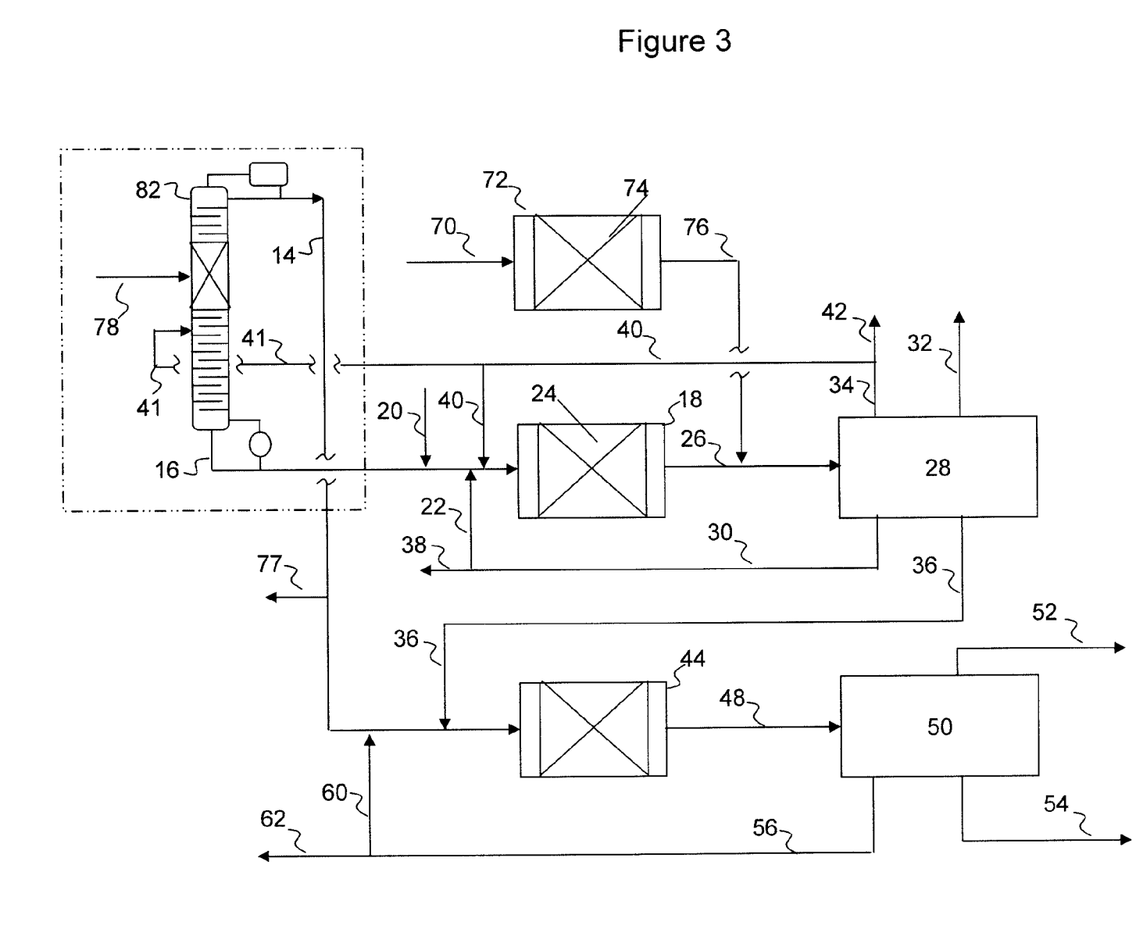
FIG. 3 is a simplified process flow diagram of a process for producing propylene according to embodiments disclosed herein.

In some embodiments, such as illustrated in FIG. 3, the mixed $C_4$ stream 40, containing unreacted normal butenes (1-butene and 2-butene) and any unreacted isobutylene, may be fed to a deisobutylenizer 80. Deisobutylenizer 80 may include, for example, a reactive distillation column 82 for concurrent hydroisomerization of 1-butene to 2-butene and separation of the 2-butene from isobutylene, such as described in U.S. Pat. Nos. 5,080,780 and 7,045,669, which are each hereby incorporated by reference.

The following examples illustrate the unique and unexpected advantages of integrating the metathesis reactor systems and the cracking reactor systems. The integration may reduce the utilities for the cracking reactor system by reactively separating the $C_4$ paraffins from the $C_4$ olefins. Further the integration may allow for similar or greater amounts of propylene to be produced from a mixed $C_4$ stream with similar or lesser amounts of valuable ethylene feedstock.

EXAMPLES

The following examples are derived from modeling techniques. Although the work has been performed, the Inventors do not present these examples in the past tense to comply with applicable rules.

For each of the simulation studies, the olefin feed is 100 kg/h. Mixed butenes feed compositions include 15% isobutene mixed with n-butenes, and n-butane is not included in the feed simulated. For the cracking simulations, isobutene is used as the $C_4$ iso-olefin, 2-methyl 2-butene is used as the model feed for the iso-pentene, 2-methyl 2-pentene is used as the model feed for the iso-hexene and 1-hexene is used as the model feed for n-$C_6$ feed.

For simulation of the cracker, a conversion reactor is used. The product distribution for the olefin cracking is obtained from "Cracking of pentenes to $C_2$-$C_4$ light olefins over zeolites and zeotypes: Role of topology and acid site strength and concentration," Bortnovsky et al., Applied Catalysis A: General, 287, 2005, 203-213. A typical product distribution for the cracking reaction using ZSM-5 as the catalyst is shown in Table 3. The example provided is for the cracking of 2-methyl 2-butene. Table 3 also provides the corresponding reaction stoichiometry that would be used in the conversion reactor simulating the cracker.

TABLE 3

A typical product distribution for the cracking reaction using ZSM-5 as the catalyst - 2-Methyl 2-Butene Cracking
Feed: 2-methyl 2-butene
Conversion: 85%

| Component | Selectivity (%) | Product Distribution (wt. %) |
|---|---|---|
| Paraffins | 7.5 | 6.38 |
| Ethane | 3 | 2.55 |
| Propane | 2.5 | 2.13 |
| n-Butane | 2 | 1.7 |
| Ethylene | 8.5 | 7.23 |
| Propylene | 34 | 28.9 |
| Butenes | 35 | 29.75 |
| 1-butene | 6.53 | 5.55 |
| trans-2-butene | 7.92 | 6.73 |
| cis-2butene | 6.11 | 5.19 |
| isobutylene | 14.44 | 12.27 |
| Pentenes | 5 | 4.25 + 15 |
| 1-pentene | 2 | 1.7 |
| 2-methyl 2-butene | — | 15 (unconverted feed) |
| trans-2-pentene | 2 | 1.7 |
| cis-2-pentene | 1 | 0.85 |
| Hexenes | 5 | 4.25 |
| 1-hexene | 0.4 | 0.34 |
| trans-2-hexene | 2.15 | 1.83 |
| cis-2-hexene | 1.00 | 0.85 |
| trans-3-hexene | 1.10 | 0.94 |
| cis-3-hexene | 0.35 | 0.30 |
| Aromatics | 5 | 4.2 |
| Benzene | 0.4 | 0.34 |
| Toluene | 2.1 | 1.79 |
| ortho-Xylene | 0.83 | 0.71 |
| meta-Xylene | 0.83 | 0.71 |
| para-Xylene | 0.84 | 0.71 |

Comparative Example 1

Baseline Conventional Metathesis

Figure 4:
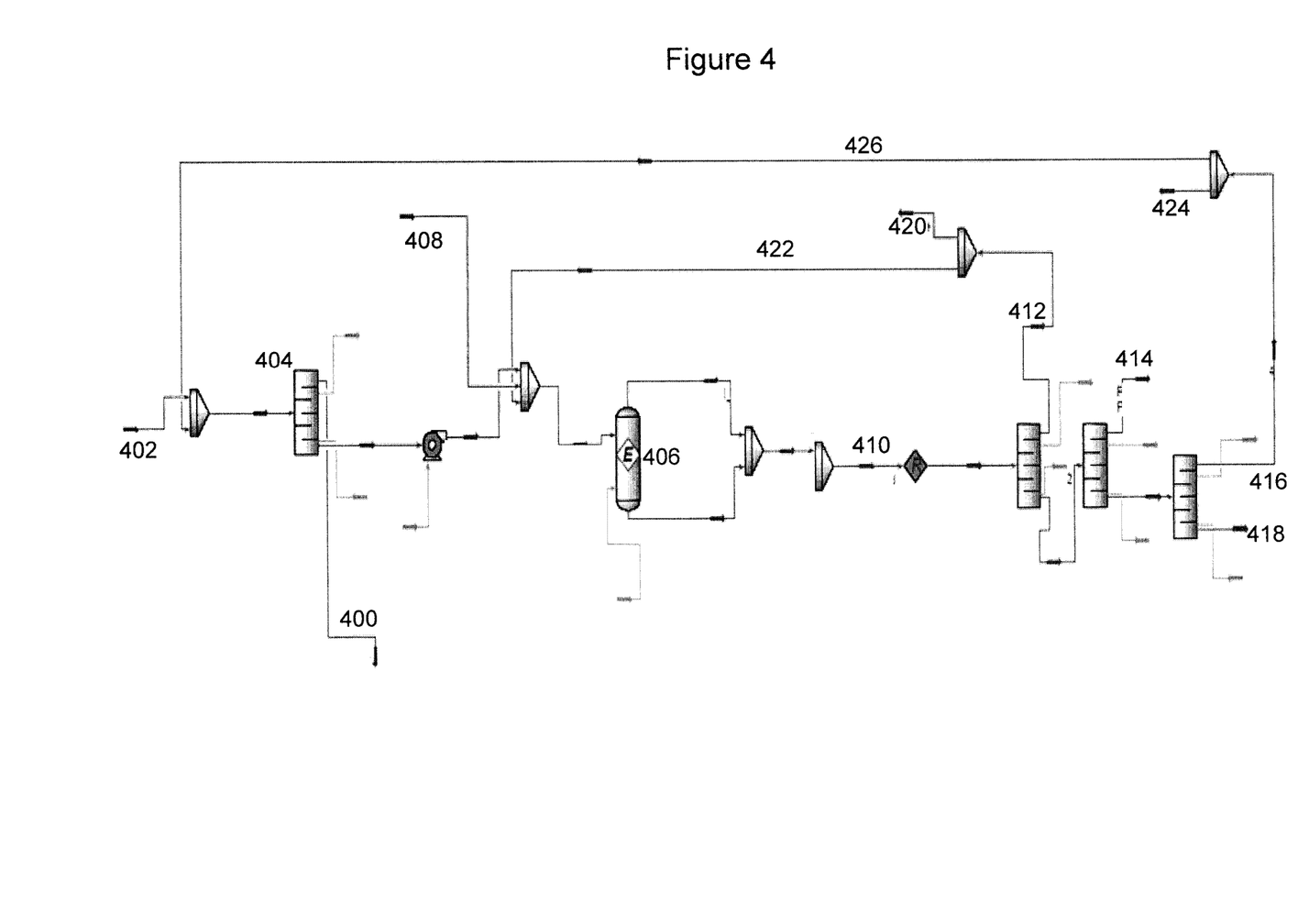
FIG. 4 is a flow diagram of a comparative metathesis process.

A conventional metathesis process is simulated. Isobutene 400 in the $C_4$ feed 402 is removed via separator 404 before the feed is sent to the conventional metathesis reactor 406. Ethylene 408 is fed to metathesis reactor 406 at a rate to maintain an ethylene to n-butene molar ratio at the inlet to the conventional metathesis reactor 406 at 1.8 (38.5 kg/h ethylene feed). An overall $C_4$ utilization of 96% and an overall $C_2$ utilization of 94% are used to simulate the metathesis reactor effluent 410, which is subsequently separated into $C_2$s 412, $C_3$s 414, $C_4$s 416, and $C_{5+}$ 418, with $C_2$ and $C_4$ purge and recycle streams 420, 422, 424, and 426. The details and results of the simulation are given in Table 4. The propylene produced is 112.4 kg/h, resulting solely from the conventional metathesis of butenes and ethylene.

TABLE 4

| | Stream | | | | | | |
|---|---|---|---|---|---|---|---|
| | 402 | 400 | 408 | 414 | 420 | 426 | 418 |
| Description | Butene Feed | Isobutylene | Ethylene | Propylene | $C_2$ Purge | $C_4$ Purge | $C_5/C_6$ Purge |
| Rate (kg/h) | 100 | 15.75 | 38.5 | 112.4 | 2.11 | 3.88 | 4.51 |

Example 1

A process similar to that illustrated in FIG. 1 is illustrated. The ethylene to n-butene ratio was held at 1.79. $C_4$ and $C_2$ utilizations of 96% and 94%, respectively, are used to simulate metathesis reactor 18. No additional $C_{4+}$ feeds are fed to cracker 44 via flow line 46, and cracker $C_4$s are recycled to fractionator 12. The details and results of the simulation are given in Table 5. The propylene produced is 128.2 kg/h, resulting from conventional metathesis and cracking.

TABLE 5

| | Stream | | | | |
|---|---|---|---|---|---|
| | 10 | 14 | 20 | 32 | 38 |
| Description | Butene Feed | Iso-butylene | Ethylene | Propylene | $C_2$ Purge |
| Rate (kg/h) | 100 | 20.73 | 40.5 | 117.2 | 2.11 |

| | Stream | | | |
|---|---|---|---|---|
| | 42 | 62 | 52 | 54 | 54 + 32 |
| Description | $C_4$ Purge | $C_5/C_6$ Purge | Ethylene | Propylene | Total Propylene |
| Rate (kg/h) | 3.82 | 0.09 | 2.71 | 11.02 | 128.22 |

Example 1 indicates that an additional 14% of propylene may be produced over the conventional metathesis process of Comparative Example 1. The integrated process, including cracking and metathesis, allows for additional processing of the isobutylene and $C_5/C_6$ products produced in the conventional metathesis to produce additional propylene, resulting in reduced purge of $C_5/C_6$ materials from the process. The cracker additionally produces a small quantity of aromatics (1.7 kg/h).

Example 2

Example 2 also simulates a process similar to that illustrated in FIG. 1, where the recycle stream from the cracker is sent back to the cracker via flow line 60, and no recycle from the cracker is sent to fractionator 12. The ethylene to n-butene ratio is maintained at 1.79. $C_4$ and $C_2$ utilizations of 96% and 94%, respectively, are used to simulate metathesis reactor 18. No additional $C_{4+}$ feeds are fed to cracker 44 via flow line 46, and cracker $C_4$s are recycled to fractionator 12. The details and results of the simulation are given in Table 6. The propylene produced is 124.6 kg/h, resulting from conventional metathesis and cracking.

TABLE 6

| Stream | | | | |
|---|---|---|---|---|
| 10 | 14 | 20 | 32 | 38 |
| Description | Butene Feed | Iso-butylene | Ethylene | Propylene | $C_2$ Purge |
| Rate (kg/h) | 100 | 15.75 | 38.5 | 112 | 2.05 |

| Stream | | | | |
|---|---|---|---|---|
| 42 | 62 | 52 | 54 | 54 + 32 |
| Description | $C_4$ Purge | $C_5/C_6$ Purge | Ethylene | Propylene | Total Propylene |
| Rate (kg/h) | 3.78 | 0.53 | 3.12 | 12.62 | 124.62 |

Example 2 indicates that an additional 11% of propylene may be produced over the conventional metathesis process of Comparative Example 1. As compared to the flow scheme of Example 1, there is a 3% decrease in propylene production rate when the cracker recycle is sent back to the cracker.

Example 3

The process configuration for this Example is the same as for Example 1 with the following differences. The ethylene to n-butene ratio is maintained at 1.0, as compared to 1.8 in Example 1, and about 50% of the isobutene in the mixed $C_4$ feed is allowed to pass through fractionator 12 to conventional metathesis reactor 18. These feed changes relax the specifications on the deisobutanizer upstream of the metathesis reactor. Additionally, isobutene is half as productive as ethylene in propylene production by metathesis, where the resulting branched $C_5$ olefin (2-methyl 2-butene) may be sent to cracker 44 via flow line 36 to produce additional light olefins. The details and results of the simulation are given in Table 7. The propylene produced is 117.1 kg/h, resulting from conventional metathesis and cracking.

TABLE 7

| Stream | | | | |
|---|---|---|---|---|
| 10 | 14 | 20 | 32 | 38 |
| Description | Butene Feed | Iso-butylene | Ethylene | Propylene | $C_2$ Purge |
| Rate (kg/h) | 100 | 11.38 | 30.2 | 103.2 | 1.17 |

| Stream | | | | |
|---|---|---|---|---|
| 42 | 62 | 52 | 54 | 54 + 32 |
| Description | $C_4$ Purge | $C_5/C_6$ Purge | Ethylene | Propylene | Total Propylene |
| Rate (kg/h) | 3.99 | 0.01 | 3.39 | 13.9 | 124.62 |

The process conditions of Example 3 result in a slight decrease in propylene production as compared to Examples 1 and 2. However, it is important to recognize the added benefit of decreased ethylene consumption and less stringent $C_4$ separations.

Example 4

The process configuration for this Example is the same as for Example 1 with the following differences. The ethylene to n-butene ratio at the entrance of the conventional metathesis reactor 18 is adjusted so that there is no net ethylene consumption in the process, i.e., the amount of ethylene fed to the conventional metathesis reactor is the same as the ethylene produced in the cracker. Additionally, as in Example 3, about 50% of the isobutene in the raffinate is allowed to pass through to the conventional metathesis reactor 18. The details and results of the simulation are given in Table 8. The propylene produced is 83.3 kg/h, resulting from conventional metathesis and cracking.

TABLE 8

| Stream | | | | |
|---|---|---|---|---|
| 10 | 14 | 20 | 32 | 38 |
| Description | Butene Feed | Iso-butylene | Ethylene | Propylene | $C_2$ Purge |
| Rate (kg/h) | 100 | 17.57 | 6.75 | 55.81 | 0.29 |

| Stream | | | | |
|---|---|---|---|---|
| 42 | 62 | 52 | 54 | 54 + 32 |
| Description | $C_4$ Purge | $C_5/C_6$ Purge | Ethylene | Propylene | Total Propylene |
| Rate (kg/h) | 3.99 | 0.03 | 6.76 | 27.54 | 83.3 |

While Example 4 results in a lower propylene production, Example 4 provides the advantage of operating without the need for an ethylene feed stream and with less stringent isobutylene separation specifications. Examples 3 and 4 illustrate the flexibility of processes according to embodiments disclosed herein to accommodate varied feed requirements suitable for both integrated and non-integrated refiners.

Comparative Example 2

Stand-Alone Cracker

Figure 5:
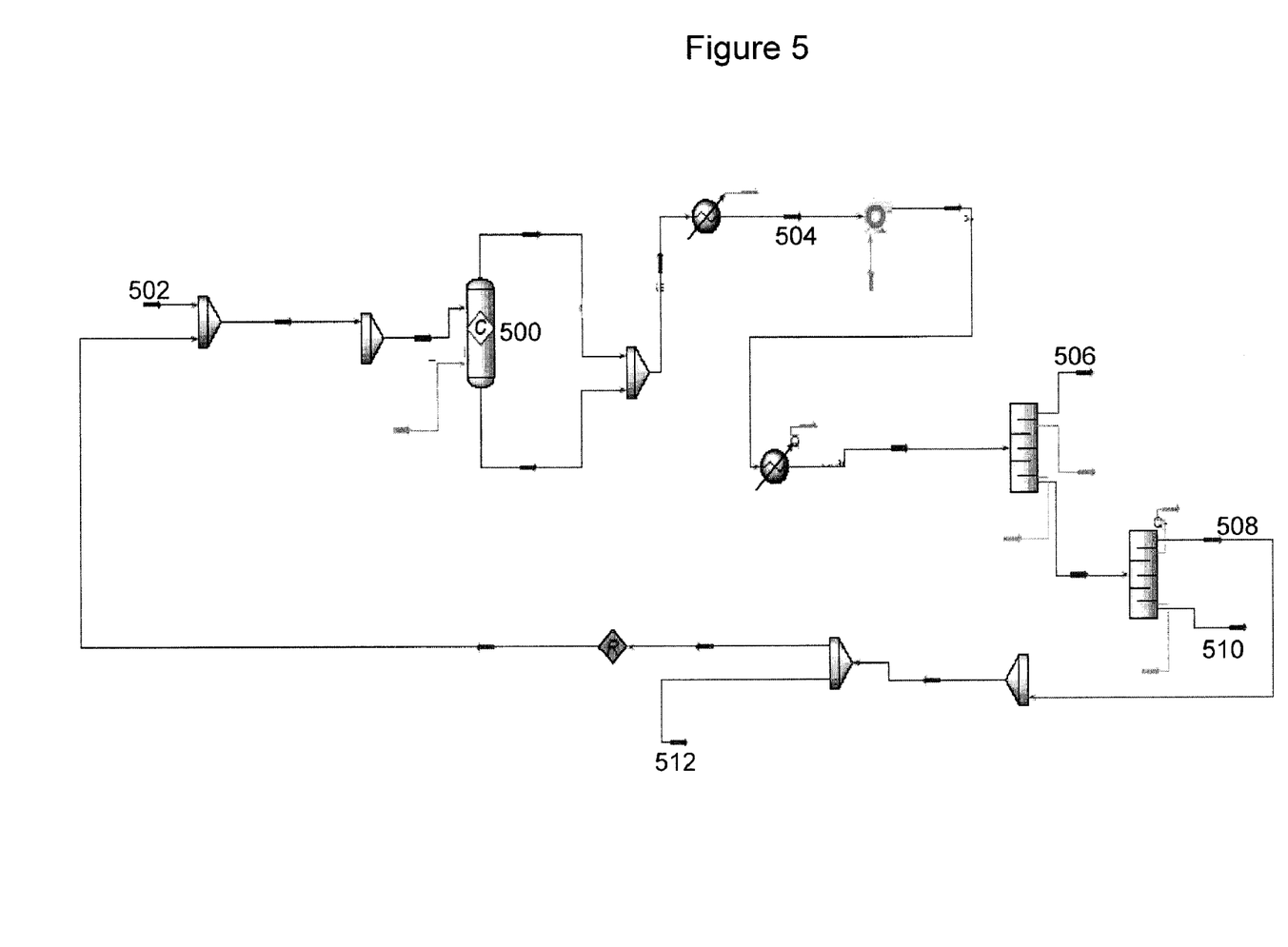
FIG. 5 is a flow diagram of a comparative cracking process.

Simulations are performed for a stand-alone cracker, similar to that illustrated in FIG. 5, utilizing different feeds for the cracker. The feeds that are used include:
a) $C_4$ raffinate (representative of n-butene and iso-butene),
b) 2-methyl 2-butene (representative of iso-pentene),
c) 1-hexene (representative of n-hexene), and
d) 2-methyl 2-pentene (representative of iso-hexene).

The feed to cracker 500 is fed via flow line 502, where effluent 504 is calculated as described above. The resulting effluent 504 is then separated to produce a $C_2/C_3$ fraction 506, a $C_4$-$C_6$ fraction 508, and an aromatics fraction 510. A portion of the $C_4$-$C_6$ fraction may be purged via flow line 512. The results of the simulations of the above feeds a-d are given in Table 9.

TABLE 9

| | | Stream | | | | |
|---|---|---|---|---|---|---|
| | | 502 | 506 | 508 | 510 | 512 |
| | | | | Description | | |
| Case | | Cracker Feed | Ethylene/ Propylene | $C_4$-$C_6$ Recycle | Aromatics | $C_4$-$C_6$ Purge |
| a: $C_4$ raffinate | Rate (kg/h) | 100 | 15.35/ 61.37 | 397.3 | 9.03 | 4.02 |
| b: 2-methyle 2 butene | Rate (kg/h) | 100 | 15.38/ 61.51 | 371.8 | 9.06 | 3.76 |

TABLE 9-continued

| | | Stream | | | | |
|---|---|---|---|---|---|---|
| | | 502 | 506 | 508 | 510 | 512 |
| | | | | Description | | |
| Case | | Cracker Feed | Ethylene/ Propylene | $C_4$-$C_6$ Recycle | Aromatics | $C_4$-$C_6$ Purge |
| c: 1-hexene | Rate (kg/h) | 100 | 15.35/ 61.39 | 392.6 | 9.03 | 3.97 |
| d: 2-methyl 2-pentane | Rate (kg/h) | 100 | 14.93/ 59.72 | 390.3 | 11.5 | 3.95 |

The results show that the propylene production rates from the different olefins are very similar. A significant difference in each of the cracker cases is that the cracker recycle rates are substantial. In each of cases a-d, the cracker recycle rate is about 3.9 times the feed flow rate. In contrast, the recycle rates for processes according to embodiments disclosed herein, such as shown by Examples 1-4 show cracker recycle rates of 8-52 kg/h, ranging from 2-13% the recycle of Comparative Examples 2a-2d.

Example 5

A process similar to that illustrated in FIG. 3 is simulated, including both auto-metathesis and conventional metathesis. The ethylene to n-butene ratio is adjusted to result in zero net ethylene consumption, similar to Example 4 above. $C_4$ and $C_2$ utilizations of 96% and 94%, respectively, are used to simulate metathesis reactor 18. The details and results of the simulation are given in Table 10. The propylene produced is 83.4 kg/h, resulting from conventional metathesis, auto-metathesis and cracking.

TABLE 10

| | Stream | | | | |
|---|---|---|---|---|---|
| | 70 | 14 | 20 | 32 | 38 |
| Description | Butene Feed | Iso-butylene | Ethylene | Propylene (auto/conventional) | $C_2$ Purge |
| Rate (kg/h) | 100 | 4.44 | 7.37 | 53.37 (16.31/37.18) | 0.27 |

| | Stream | | | | |
|---|---|---|---|---|---|
| | 42 | 62 | 52 | 54 | 54 + 32 |
| Description | $C_4$ Purge | $C_5$/$C_6$ Purge | Ethylene | Propylene | Total Propylene |
| Rate (kg/h) | 3.86 | 0.02 | 7.37 | 29.94 | 83.4 |

As described above, embodiments disclosed herein provide for the integrated metathesis and cracking of $C_4$-$C_6$ feeds. Integration of the cracker into the metathesis process clearly shows a propylene yield advantage. Other advantages have also been recognized utilizing process variations, where the flexibility of the processes disclosed herein may provide significant cost advantages for refiners having a limited ethylene supply. Additionally, processes according to embodiments disclosed herein may allow for the production of high purity propylene from $C_4$ olefins at low cost and low energy consumption.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed is:

1. A process for the production of propylene, the process comprising:
   contacting a mixed-$C_4$ stream comprising n-butenes, isobutylene, and paraffins with a metathesis catalyst whereby auto-metathesis occurs including the reaction of isobutylene with n-butenes to form an auto-metathesis product comprising ethylene, propylene, and heavier olefins including unreacted isobutylene and paraffins;
   fractionating the auto-metathesis product into at least four fractions including an ethylene fraction, a propylene fraction, a $C_{5+}$ fraction, and a $C_4$ fraction containing n-butenes, isobutylene, and paraffins;
   fractionating the $C_4$ fraction into at least two fractions including a light $C_4$ fraction comprising isobutylene and a heavy $C_4$ fraction comprising n-butenes and paraffins;
   contacting at least a portion of the heavy $C_4$ fraction and ethylene with a metathesis catalyst to form a metathesis product comprising ethylene, propylene, $C_{4+}$ olefins, and paraffins;
   feeding the metathesis product to the fractionating the auto-metathesis product;
   cracking the $C_{5+}$ fraction to produce a cracking product comprising ethylene, propylene, and heavier hydrocarbons; and
   fractionating the cracking product into at least two fractions including a light fraction comprising propylene and a fraction comprising $C_5$ to $C_6$ hydrocarbons.

2. The process of claim 1, further comprising feeding the light $C_4$ fraction to the cracking.

3. The process of claim 1, further comprising recycling at least a portion of the fraction comprising $C_5$ to $C_6$ hydrocarbons to the cracking.

4. The process of claim 1, wherein the auto-metathesis catalyst comprises at least one of a Group VIA and a Group VIIA metal oxide.

5. The process of claim 4, wherein the auto-metathesis catalyst is supported on at least one of silica, alumina, zirconia, and zeolite.

6. The process of claim 1, wherein the auto-metathesis catalyst comprises tungsten oxide on a silica support.

7. The process of claim 1, wherein the metathesis catalyst comprises at least one of a Group VIA and a Group VITA metal oxide.

8. The process of claim 7, wherein the metathesis catalyst is supported on at least one of silica, alumina, zirconia, and zeolite.

9. The process of claim 1, wherein the metathesis catalyst comprises tungsten oxide on a silica support.

10. The process of claim 1, wherein the metathesis catalyst is admixed with an isomerization catalyst.

11. The process of claim 10, wherein the isomerization catalyst comprises at least one of a Group IA and a Group IIA metal oxide.

12. The process of claim 10, wherein the isomerization catalyst comprises at least one of magnesium oxide, calcium oxide, and combinations thereof.

13. The process of claim 1, wherein the metathesis catalyst is formulated to have both a metathesis reaction function and a double bond isomerization function.

14. The process of claim 13, wherein the n-butenes comprise 1-butene and 2-butene, the process further comprising:

contacting at least one of the $C_4$ fraction and the heavy $C_4$ fraction with the isomerization catalyst to convert at least a portion of the 1-butene to 2-butene.

15. The process of claim 1, further comprising at least one of:

recycling at least a portion of the ethylene fraction to the metathesis contacting;

recycling ethylene from the cracking product to the metathesis contacting; and feeding a hydrocarbon stream containing ethylene to the metathesis contacting.

16. The process of claim 1, wherein a ratio of ethylene to n-butene in a feed to the metathesis contacting is in a range from about 0.5 to about 2.5.

17. The process of claim 16, wherein a ratio of ethylene to n-butene in a feed to the metathesis contacting is in a range from about 0.1 to about 2.0.

18. The process of claim 1, wherein the mixed-$C_4$ fraction further comprises butadiene, the process further comprising hydrogenating at least a portion of the butadiene.

* * * * *